United States Patent
Desai et al.

(10) Patent No.: US 12,179,356 B2
(45) Date of Patent: Dec. 31, 2024

(54) VOICE-ACTIVATED, COMPACT, AND PORTABLE ROBOTIC SYSTEM

(71) Applicant: Georgia Tech Research Corporation, Atlanta, GA (US)

(72) Inventors: Jaydev P. Desai, Atlanta, GA (US); Seokhwan Jeong, Atlanta, GA (US); Phillip Tran, Atlanta, GA (US); Xuefeng Wang, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 436 days.

(21) Appl. No.: 17/433,367

(22) PCT Filed: Mar. 4, 2020

(86) PCT No.: PCT/US2020/020954
§ 371 (c)(1),
(2) Date: Aug. 24, 2021

(87) PCT Pub. No.: WO2020/180965
PCT Pub. Date: Sep. 10, 2020

(65) Prior Publication Data
US 2022/0143826 A1    May 12, 2022

Related U.S. Application Data

(60) Provisional application No. 62/813,200, filed on Mar. 4, 2019.

(51) Int. Cl.
*B25J 9/16*    (2006.01)
*B25J 9/00*    (2006.01)
(Continued)

(52) U.S. Cl.
CPC .......... *B25J 9/1615* (2013.01); *B25J 9/0006* (2013.01); *B25J 9/0015* (2013.01); *B25J 9/1075* (2013.01);
(Continued)

(58) Field of Classification Search
CPC ...... B25J 9/1615; B25J 9/0006; B25J 9/0015; B25J 9/1075; B25J 9/1612; B25J 9/1633; B25J 13/003; B25J 15/0683; A61F 2/586
See application file for complete search history.

(56) References Cited

U.S. PATENT DOCUMENTS 5,025,502 A * 6/1991 Raymond ............... B63C 11/04
                                                        2/16
6,182,293 B1 * 2/2001 Mustin ............. A41D 19/01547
                                                        2/163
(Continued)

FOREIGN PATENT DOCUMENTS

KR    20-0349089       4/2004
WO    WO 2017/072463 A1   5/2017

OTHER PUBLICATIONS

European Patent Office: "Supplementary European Search Report"; Mar. 1, 2024; Search Report in related European Case.

*Primary Examiner* — Jaime Figueroa
*Assistant Examiner* — Sihar A Karwan
(74) *Attorney, Agent, or Firm* — Bryan W. Bockhop; Bockhop Intellectual Property Law, LLC (57) ABSTRACT

In a joint movement device (100) for selective flexion and extension of a joint (20), a tendon (120) is disposed adjacent to the first and second joint members. A tendon securing
(Continued)

device (112) is secured to the second joint member (12), the tendon (120) being secured to the tendon securing device (112). At least one phalange ring (110) is secured to a joint member and includes a tending routing mechanism (113) configured to route the tendon through the phalange ring (110). An actuator (140) is coupled to the tendon (120) and pulls the tendon (120) inwardly to cause the joint (20) to flex. An elastic member (130) is coupled to the phalange ring (110) and tendon securing device (112) and applies an extension force thereto, thereby causing the joint (20) to extend when the actuator (140) releases the tendon (120).

25 Claims, 6 Drawing Sheets (51) Int. Cl.
  *B25J 9/10* (2006.01)
  *B25J 13/00* (2006.01)
  *B25J 15/06* (2006.01)
(52) U.S. Cl.
  CPC ........... *B25J 9/1612* (2013.01); *B25J 9/1633* (2013.01); *B25J 13/003* (2013.01); *B25J 15/0683* (2013.01)

(56) References Cited

U.S. PATENT DOCUMENTS

| | | | |
|---|---|---|---|
| 6,427,248 | B1 | 8/2002 | Albert |
| 6,675,392 | B2 * | 1/2004 | Albert .................. A63B 71/148 2/161.1 |
| 2001/0044950 | A1 * | 11/2001 | Sajovic ............ A41D 19/01547 2/168 |
| 2003/0005507 | A1 * | 1/2003 | Litke .................... A63B 71/148 2/161.4 |
| 2006/0094989 | A1 * | 5/2006 | Scott ....................... A61F 2/586 602/22 |
| 2006/0282936 | A1 * | 12/2006 | Olson .............. A41D 19/01558 2/161.7 |
| 2009/0089909 | A1 * | 4/2009 | Castro .................. A63B 71/148 2/163 |
| 2011/0179597 | A1 * | 7/2011 | Habboush ............... B08B 15/04 29/428 |
| 2013/0085325 | A1 * | 4/2013 | Fuller ...................... A61M 1/76 600/102 |
| 2017/0168565 | A1 * | 6/2017 | Cohen .................. A61B 5/0022 |
| 2019/0010685 | A1 * | 1/2019 | Piquant ................... E03C 1/308 |
| 2019/0084762 | A1 * | 3/2019 | Fujihara ............... B25J 15/0061 |
| 2019/0314103 | A1 * | 10/2019 | Norris ................... A61M 1/774 |

* cited by examiner

VOICE-ACTIVATED, COMPACT, AND PORTABLE ROBOTIC SYSTEM

CROSS-REFERENCE TO RELATED APPLICATION(S)

This application claims the benefit of U.S. Provisional Patent Application Ser. No. 62/813,200, filed Mar. 4, 2019, the entirety of which is hereby incorporated herein by reference.

BACKGROUND OF THE INVENTION

1. Field of the Invention

The present invention relates to joint flexion and extension systems and, more specifically, to a voice-activated robotic exoskeletal flexion and extension system.

2. Description of the Related Art

Spinal cord injury (SCI) is a neurological disorder that results in a variety of disabilities, examples of which include spasticity, cardiac dysfunction, and complete loss of motor function and control of hand movement. The inability of SCI patients to voluntarily move their hands decreases both their quality of life and their independence. Stroke patients have similar difficulties. Thus, much effort has been dedicated to realizing methods for improving and/or restoring hand function in those with impaired hand function.

Physical therapy and rehabilitation through functional hand exercises in the form of activities of daily living can facilitate the recovery of hand function in people with degraded or nonexistent motor control, such as SCI and stroke patients. Since the ability of the patient to perform hand movements independently can be compromised, assistance must be provided to the patient to successfully accomplish rehabilitation tasks. Traditionally, such assistance is in the form of a therapist moving a patient's hand and fingers to exercise the muscles. However, such therapy requires direct therapist involvement with a single patient during an entire therapy session. fingers to exercise the muscles. However, such therapy requires direct therapist involvement with a single patient during an entire therapy session.

Several robotic rehabilitation devices have been developed to assist both patients and therapists during rehabilitation. Also, permanent assistive devices for carrying out activities of daily living (ADL) have been developed. However, development of such robotic devices is still in an early stage. One type of such a device is a robotic rehabilitation exoskeleton that is attached to a patient's hand and that causes a predetermined pattern of movement in the hand.

Rehabilitation exoskeletons can generally be classified into two broad categories based on the design and actuation technique: traditional rigid kinematic structures and soft robotic systems. Traditional exoskeletons typically feature a rigid construction and utilize gears, linkages, and pulleys that are directly integrated into the exoskeleton itself to drive actuation. A disadvantage of these devices is that movement restriction is caused by bulky designs and increased exoskeleton weight.

One potential solution to this disadvantage is through soft robotics. Soft robotic exoskeletons conform to the shape of the hand and use a minimal number of moving components. This reduces the size, weight, and complexity of the design and can improve range-of-motion (ROM) due to the decreased number of restrictive elements placed on the hand.

Various methods of actuation are used in soft exoskeletons, such as tendon-drive, pneumatic, and hydraulic systems. However, current actuation designs tend not to be portable and tend to restrict overall ROM of the patient. Pneumatic-driven and hydraulic-driven systems require relatively large and noisy pumps to function properly. In tendon-driven systems, the main design obstacle is the implementation of bi-directional actuation for flexion and extension of the fingers. Current tendon-drive designs utilize pulley systems with a large footprint, thus necessitating an immobile actuation block.

To enable exoskeleton control, rehabilitation exoskeletons utilize many different methods such as electromyography (EMG), vision-based classification, and manual control by another person. A common disadvantage among these control strategies is the requirement of a static computing setup connected to the exoskeleton, thus restricting the mobility of the user and limiting the ROM of the user's upper body. Other important aspects include the user-friendliness, intuition, and implementation required for exoskeleton control. EMG-based control may be difficult to implement in SCI patients as a result of required nerve connections having been severed, thus requiring biosensor inputs from nerves not directly connected to the hand, such as the shoulder. EMG is also susceptible to external noise and signal recognition of EMG can differ between SCI patients. Manual control does not require much setup but it is not intuitive because there may be a disconnect between user intent and device actuation wherein the user is indirectly controlling the exoskeleton through another person.

Therefore, there is a need for a robotic exoskeleton system that has a minimal impact on range of motion and that can operate without continuous direct therapist involvement.

SUMMARY OF THE INVENTION

The disadvantages of the prior art are overcome by the present invention which, in one aspect, is a joint movement device for selective flexion and extension of a joint, in which the joint has a first joint member having a proximal end and an opposite distal end and a second joint member having a proximal end and an opposite distal end. The joint couples the distal end of the first joint member to the proximal end of the second joint member so that the second joint member is in a flexural relationship to the first joint member. A tendon, having a first end and an opposite second end, is disposed adjacent to a selected side of the first joint member and the second joint member. A tendon securing device is secured to the distal end of the second joint member to which the tendon is secured. At least one phalange ring is secured to the first joint member. The at least one phalange ring and tendon securing device include a tending routing mechanism configured to route the tendon from the tendon securing device through the at least one phalange ring. An actuator is in a fixed relationship with the first joint member and is coupled to the tendon. The actuator is configured to selectively pull the tendon inwardly thereto, thereby causing the joint to flex. An elastic member is coupled to the at least one phalange ring and the tendon securing device and is configured to apply an extension force thereto, thereby causing the joint to extend when the actuator releases the tendon.

In another aspect, the invention is a robotic exoskeleton configured for use with a plurality of different fingers of a hand. Each finger has at least one joint including a first joint member having a proximal end and an opposite distal end and a second joint member having a proximal end and an opposite distal end. The second joint member is in a flexural relationship to the first joint member. The robotic exoskeleton includes a plurality of joint movement devices. Each of the plurality of joint movement devices is secured to a different corresponding finger of the hand. Each joint movement device is configured to cause the corresponding finger to move in a predetermined manner. Each of the plurality of joint movement devices includes: a first tendon, having a first end and an opposite second end, disposed adjacent to a selected side of the first joint member and the second joint member; a tendon securing device secured to the distal end of the second joint member to which the tendon is secured; a first phalange ring secured to the first joint member and a second phalange ring secured to the second joint member, the first phalange ring, the second phalange ring, and the tendon securing device including a tending routing mechanism configured to route the tendon from the tendon securing device through the first phalange ring and the second phalange ring; an actuator in a fixed relationship with the first joint member and coupled to the tendon, the actuator configured to selectively pull the tendon inwardly thereto, thereby causing the joint to flex, the actuator including a tendon shortening mechanism configured to shorten a portion of the first tendon between the first phalange ring and the tendon securing device; and an elastic member coupled to the first phalange ring, the second phalange ring, and the tendon securing device and configured to apply an extension force thereto, thereby causing the joint to extend when the actuator releases the tendon. A controller is in control communication with each actuator and is configured to respond to a plurality of different voice commands regarding flexion and extension of each joint.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

A preferred embodiment of the invention is now described in detail. Referring to the drawings, like numbers indicate like parts throughout the views. Unless otherwise specifically indicated in the disclosure that follows, the drawings are not necessarily drawn to scale. The present disclosure should in no way be limited to the exemplary implementations and techniques illustrated in the drawings and described below. As used in the description herein and throughout the claims, the following terms take the meanings explicitly associated herein, unless the context clearly dictates otherwise: the meaning of "a," "an," and "the" includes plural reference, the meaning of "in" includes "in" and "on."

To overcome limitations of existing systems, one embodiment of the invention employs a tendon-actuated, voice-controlled soft robotic exoskeleton with 4 degrees-of-freedom for improving hand function in SCI patients. The actuation mechanism utilizes both active and passive actuation techniques to create a compact and lightweight system that can be carried on the forearm to improve patient mobility. Additionally, the use of voice control through a smartphone app removes the need for bulky control units, further increasing the portability of the exoskeleton and providing an intuitive control interface.

Figure 1A:
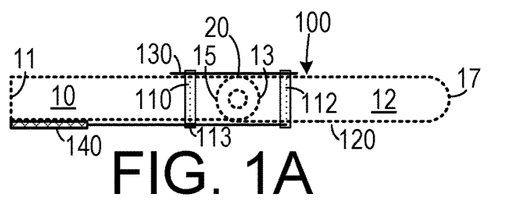
FIGS. 1A-1B are schematic diagrams showing one representative embodiment of a joint movement device for a joint with two joint members.
Figure 1B:
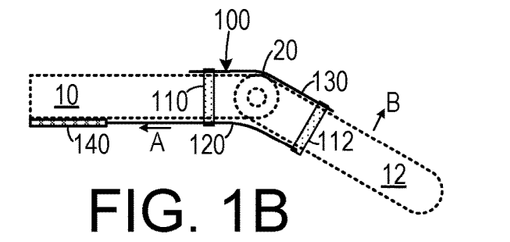

As shown in FIGS. 1A and 1B, one representative embodiment of the invention is a joint movement device 100 for selective flexion and extension of a joint 20 having a first joint member 10 having a proximal end 11 and an opposite distal end 13 and a second joint member 12 having a proximal end 15 and an opposite distal end 17 and the joint coupling the distal end 13 of the first joint member 10 to the proximal end 15 of the second joint member 12 so that the second joint member 12 is in a flexural relationship to the first joint member 10.

A first tendon 120 is disposed adjacent to a selected side of the first joint member 10 and the second joint member 12. When the first joint member 10 and the second joint member 12 are parts of a finger, the selected side can be either the palmar side or the dorsal side of the finger.

A first phalange ring 110 is secured to the first joint member 10 and a tendon securing device 112 (which could have the configuration of a second phalange ring, or a thimble-like cap) is secured to the second joint member 12. The phalange ring 110 and tendon securing device 112 each have a tending routing mechanism 113 configured to route the tendon from the tendon securing device 114 through the phalange ring 110. In one embodiment, the routing mechanism 113 includes a passage that is lined with a poly (tetrafluoroethylene) (e.g., Teflon®) liner so as to minimize friction on the tendon 120. (Also, other tubing used to route and house portions of the tendon 120 can include poly (tetrafluoroethylene) to minimize friction.)

An actuator 140 is placed in a fixed relationship with the first joint member 10 and is coupled to the tendon 120. As shown in FIG. 1B, the actuator 140 acts as a shortening mechanism that shortens (as in the direction of arrow A) a portion of the first tendon 120 between the first phalange ring 110 and the tendon securing device 112, thereby causing the joint 20 to flex. An elastic member, such as a nickel titanium alloy (such as Nitinol) wire 130, is coupled to the first phalange ring 110 and the tendon securing device 114 so as to apply an extension force (as in the direction of arrow B), which causes the joint 20 to extend when the actuator 140 releases the tendon.

Figure 2A:
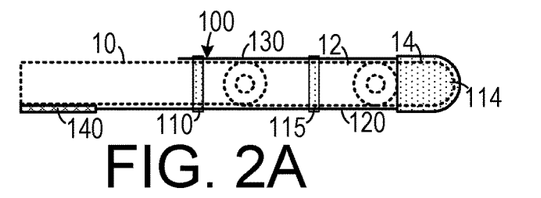
FIGS. 2A-2B are schematic diagrams showing one representative embodiment of a joint movement device for a joint with three joint members.
Figure 2B:
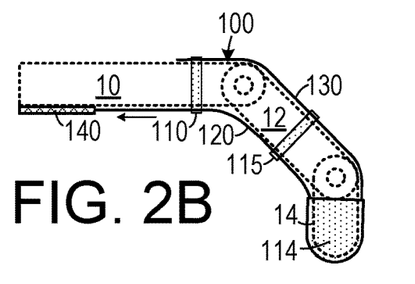

In certain embodiments, as shown in FIGS. 2A and 2B, the joint movement device 100 can be adapted for use with a finger-type joint that includes a third joint member 14. In such an embodiment, a thimble-like cap 114 can act as a tendon securing device while a second phalange ring 115 can be used to route the tendon 120.

Figure 3:
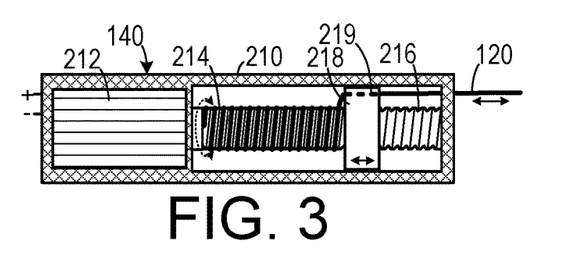
FIG. 3 is a schematic diagram showing one representative embodiment of an actuator.

In one embodiment, as shown in FIG. 3, the actuator 140 includes a housing 210 that holds a motor 212 (such as an electric motor) therein. A threaded member 214 is rotated by the motor 212 and includes a continuous spiral root 216 having a pitch corresponding to the dimeter of the tendon 120. A nut 218 is threaded onto the threaded member 214 and is held by the housing 210 so that when the motor 212 rotates the threaded member 214, the nut 218 moves laterally along the threaded member 214 in a direction corresponding to the direction of rotation. The tendon 120 runs through a passage 218 defined by the nut 218 and is wound around the threaded member 214 as it rotates in a first direction. This pulls the tendon 120 into the housing 210 and the tendon 120 is wrapped around the root 216 of the threaded member 214. When the threaded member 214 rotates in the opposite direction, the tendon 120 is unwrapped from the root 216 and a portion of it is released from the housing 210.

Figure 4A:
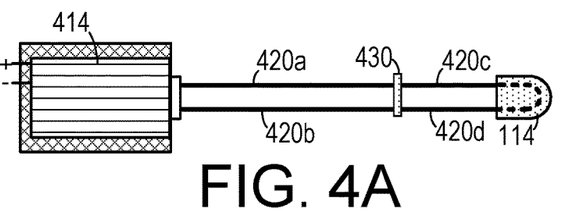
FIGS. 4A-4B are schematic diagrams showing an alternate embodiment of an actuator.
Figure 4B:
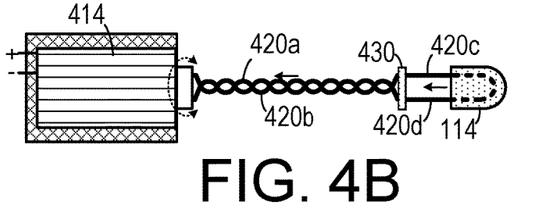

In another embodiment, as shown in FIGS. 4A and 4B, the tendon includes first portion 420a and a second portion 420b, which are attached to the spindle of a motor 414 and which are separated by a tendon separator 430, a third portion 420c and a fourth portion 420d, which are attached to the cap 114. As the motor 414 causes the spindle to spin in a first direction, the first portion 420a and the second portion 420b twist about each other, which causes the third portion 420c and the fourth portion 420d to draw in and effectively shorten. Spindle rotation in the opposite direction releases the tendon for joint extension.

Figure 5:
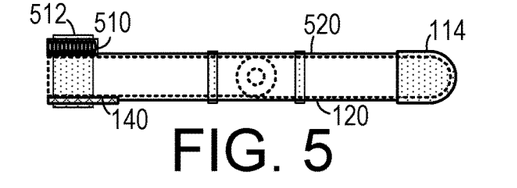
FIG. 5 is a schematic diagram showing an embodiment employing a spring-type elastic member.

In one alternative embodiment, as shown in FIG. 5, the elastic member can include a spring 510 that is affixed to the joint via a strap 512 and that is coupled to a cord 520 that is coupled to the cap 114 and that is disposed on a side of the joint opposite from the tendon 120. The spring maintains the cord 520 under tension for joint extension when the actuator 140 releases the tendon 120.

Figure 6:
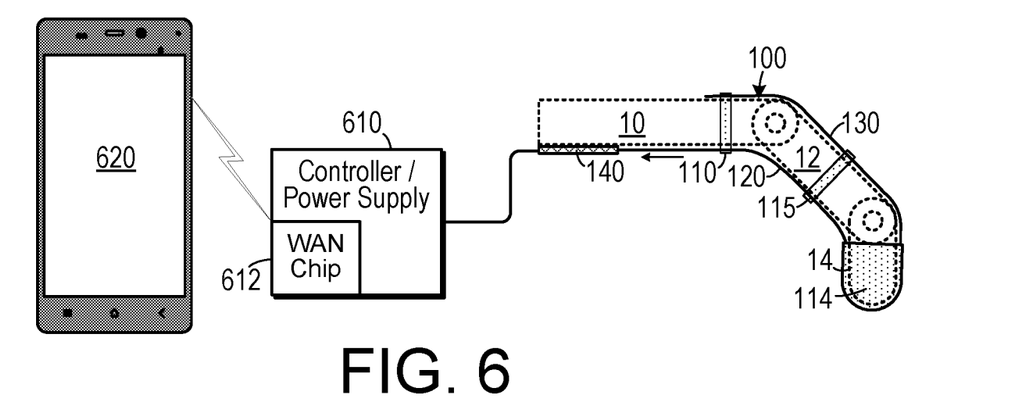
FIG. 6 is a schematic diagram showing a joint movement system employing voice activation.

As shown in FIG. 6, a controller 610 applies control voltages to the actuator 140. The controller 610 can include a wireless chipset 612 (e.g., a Bluetooth® chipset) to transmit voice and other commands from a wireless device 620 (e.g., a smart phone, a tablet, a laptop, a dedicated device, etc.) to the actuator 140. This allows a user to speak commands regarding the flexing of the joint into the wireless device 620 and the controller 610 then generates control voltages to the actuator. For example, if a plurality of joint movement devices 100 are used as a patient's hand robotic exoskeleton, then the patient can speak voice commands into the wireless device 620 to effect a hand exercise routine.

Figure 7A:
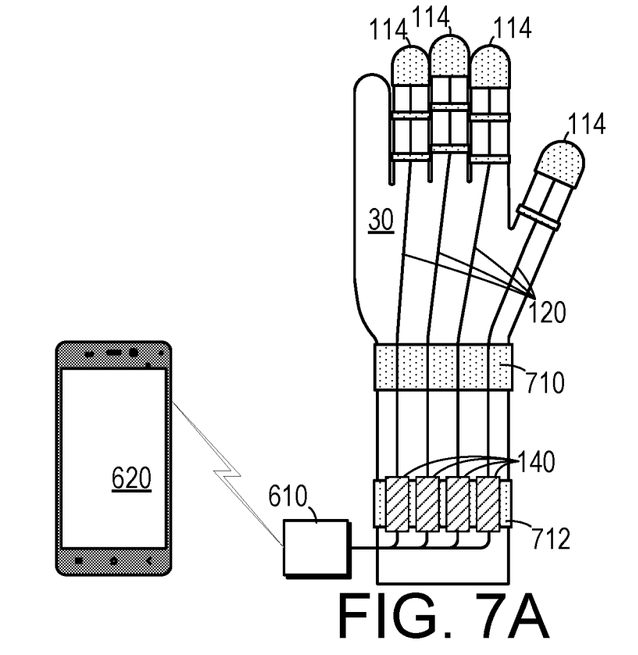
FIGS. 7A-7B are schematic diagrams showing a palm and a back of a hand wearing a robotic exoskeleton system.
Figure 7B:
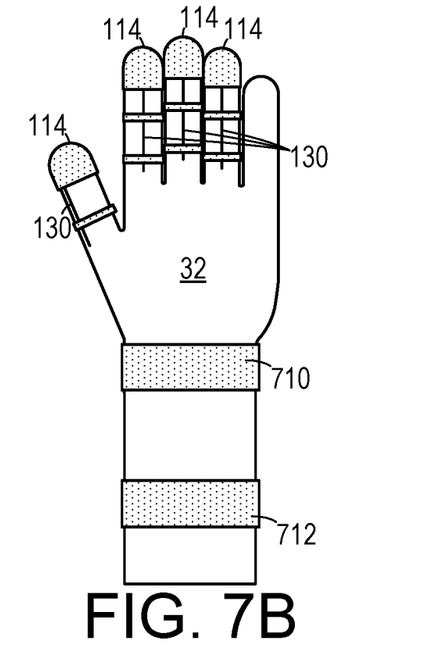

Such a hand exercise robotic exoskeleton system is shown in FIGS. 7A and 7B, which shows a view of the palm 30 and the back 32 of the patient's hand. This embodiment employs a routing strap 710 to route the tendons 120 and an actuator strap 712 to hold the actuators 140 in a fixed relationship with the patient's hand. The components of the exoskeleton system can be embedded in a glove for easy application to the patient.

In this embodiment, the wireless device can be programmed to effect predetermined actions in response to specific voice commands. Such commands could require the fingers to move in a certain way, such as: pinching, grabbing or grasping an object, or to open. Different types of objects can be specified. For example, the types of objects could include: a ball, a pen, a block, a coin or a checker. A certain type of movement applied to a certain object will result in a specific movement by the fingers. The voice commands may also include a command to "Stop Listening" and a command to "Resume Listening." The "Stop Listening" command will prevent spurious movements due to background conversations.

Figure 8:
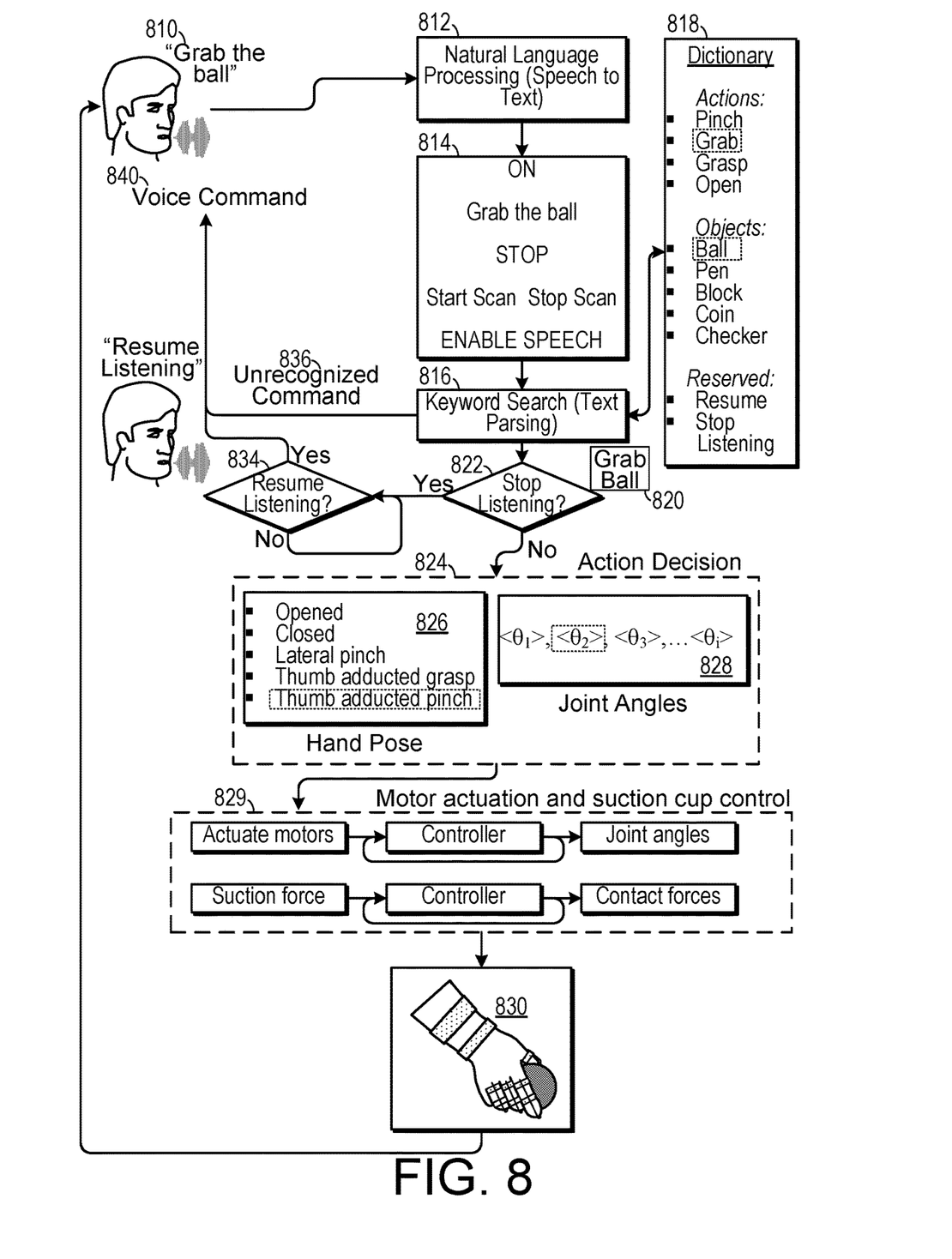
FIG. 8 is a flow diagram demonstrating a method of actuating an exoskeleton using voice commands.

In one example, as shown in FIG. 8, the user says "Grab the ball" 810 which causes the wireless device first to transform the speech input to corresponding text 812. The command is deciphered 814 and keywords from the command are parsed 816 by accessing a dictionary 818. Once the command is understood, the system begins a "Grab Ball" routine 820 and makes an action decision 824 that includes taking predetermined actions directing the exoskeleton to move into a specific hand pose 826 with the joints at predetermined joint angles 828. Motor actuation and suction cup control 829 apply the actuation force to the controller to achieve the desired joint angles and apply desired suction forces to the controller to achieve the desired level of contact force (which will be described in more detail below), respectively. Next, the commands are transformed to control voltages to the actuators that cause the exoskeleton 830 to move accordingly. Once the action is complete, the system returns to a state in which it awaits another command 840. If the result of the Keyword Search is that the command is not recognized 836, the system will return to the state in which it awaits another command 840. This will also happen if the system has been put in a "Stop Listening" state 822 and has been commanded to "Resume Listening" 834.

Figure 9A:
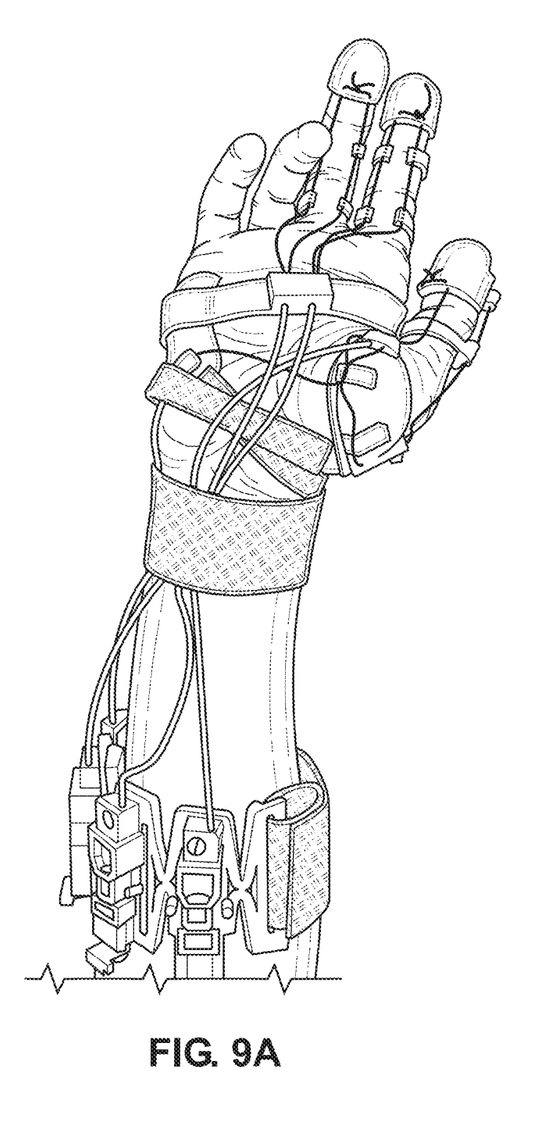
FIGS. 9A-9B are a palm view and a back-hand view of an experimental embodiment of an exoskeleton system applied to a human hand.
Figure 9B:
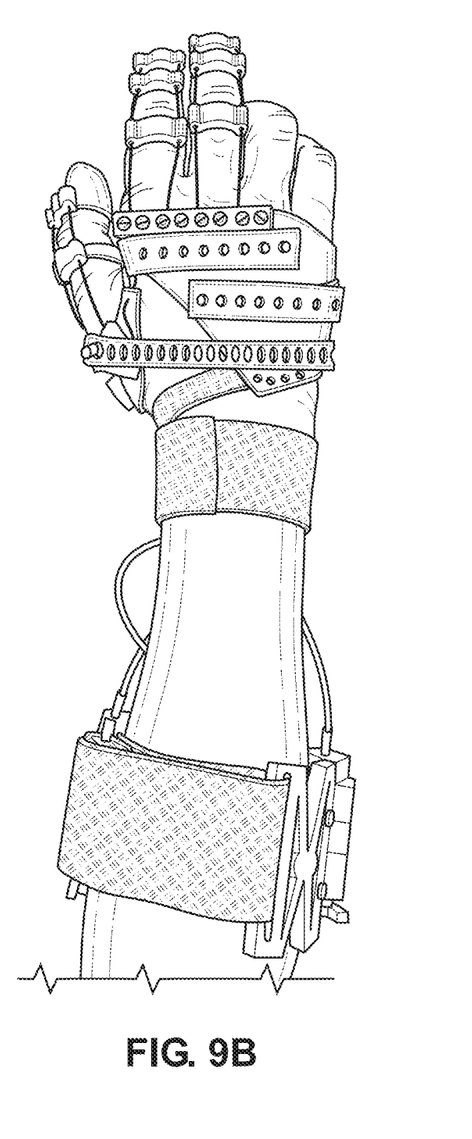

Extrinsic tendons located in the forearm are the main contributors for generating finger motion in the human hand. One experimental embodiment is shown in FIGS. 9A and 9B, which shows the palm side of an exoskeleton in FIG. 9A and a back hand side in FIG. 9B. This experimental embodiment utilizes a partially biomimetic tendon routing strategy through underactuation to achieve a simple yet effective finger flexion mechanism.

In the human hand, the flexor digitorum profundus tendons are responsible for the concurrent flexion of the metacarpophalangeal (MCP), proximal interphalangeal (PIP), and distal interphalangeal (DIP) joints in the index finger and the middle finger. This action is mimicked by the flexor tendon pairs in the experimental embodiment. The exotendons are organized in pairs to prevent force imbalance and improve stability during actuation.

The human thumb can be treated as a multi-degree of freedom (DoF) actuator that can perform many complex movements. This is mainly due to the carpometacarpal (CMC) joint, which allows for abduction and adduction to create opposable thumb movement. The adduction movement can be generated by a single tendon. The thumb is also capable of flexion through the action of the flexor pollicis longus tendon. This tendon is replicated by the thumb flexor tendon, which passes across the MCP and interphalangeal (IP) joints. Force transmission may be difficult to evenly distribute for CMC movement because of the non-uniform shape of the thenar eminence of the thumb.

To prevent attachment point shift, the adduction tendon in the experimental embodiment is wrapped around the thenar eminence. Thus, when actuated, the exotendon will tighten around the thenar eminence to distribute the contact force for improved stability.

The tendon-driven actuation used in the exoskeleton system can generate only unidirectional actuation. To implement finger flexion and extension, either active or passive actuation can be utilized. For active extension and flexion, each DoF would require two actuators to control both extension and flexion. This necessitates precise coordination of simultaneous tendon actuation to avoid interference between the extension and flexion movements. Thus, to avoid increasing the number of actuators and to decrease system complexity, passive actuation can be used for finger extension. In passive actuation, mechanical components such as a spring can be connected to the extension tendon in series and provide pretension to support extension. However, this can cause discomfort. Therefore, the passive component can be connected to the finger in parallel, which provides a force perpendicular to the finger without stress on the finger joints.

One experimental embodiment employs a passive backbone with nickel titanium alloy wires. The wires can be placed along the dorsal aspect of the index finger, middle finger, and thumb and are housed in the phalange rings. The nickel titanium alloy wires are superelastic and can withstand large strain. Therefore, the wires can withstand the high curvature bending caused by flexion of each joint without permanent deformation. The nickel titanium alloy wires mimic the function of the extensor digitorum communis tendon in the index finger and middle finger and the extensor pollicis longus tendon in the thumb to provide a compact flexion mechanism. As the actuator releases tendon tension, the nickel titanium alloy wire backbones exert torque on the finger joints to extend the finger to a predetermined resting posture.

Additionally, the backbone actuation mechanism employing superelastic wires inherently removes the problem of hyperextension. The backbone will return to its initial position upon tendon release by the actuator and so long as the fingers are not placed in a hyper-extended posture during device setup, the backbone will not over-rotate the joints. Also, this device can be used as a rehabilitative/assistive device for stroke patients. However, since stroke patients often have inherently closed hands, the tendons can run along the back sides of their hands (essentially, the device is flipped back-to-front) so that the tendons will pull the fingers into an open position.

The primary wearable components of the experimental embodiment (as shown in FIGS. 9A and 9B) can be fabricated using a deformable, low-friction 3D-printed plastic (such as, Durable Resin, available from FormLabs) and can be customized to the specifications of each user. The primary components consist of the phalange rings, CMC sleeve, and palm shell. Due to the deformability of the plastic, the phalange rings are able to be sized slightly smaller than the user's fingers to ensure a secure fit. Each ring routes the exotendons (which, in the experimental embodiment, were made from Hercules PE Braided Spectra, available from HerculesPro.com) along the sides of the finger to reduce obstruction of the palmar aspect of the finger, which can improve grasping and tactile sensation. The rings route the nickel titanium alloy wires slightly offset from the dorsal aspect of the fingers to prevent direct contact between the wires and the fingers during motion. The cap is thimble-shaped to wrap around the entire fingertip and made of 3D-printed plastic with a higher surface friction coefficient (such as, Elastic Resin, available from FormLabs, Inc.) on the palmar aspect of the fingertip to improve grip. The CMC sleeve is 3D-printed in a single piece and fits around the thenar eminence of the thumb. The adductor tendon routing strategy takes advantage of the structure of the CMC sleeve to provide force distribution around the thenar eminence during actuation to increase motion stability. The CMC sleeve decouples the flexion/extension motion of the thumb from adduction/abduction by directly connecting the thumb flexion tendon to the sleeve as well as anchoring the thumb extension nickel titanium alloy wires to the sleeve itself. Thus, flexion and extension of the thumb occurs relative to the CMC movement to prevent interference between the two DoFs of the thumb.

The secondary wearable components of the exoskeleton are the nickel titanium alloy wires and silicone bands (such as, Dragon Skin 30, available from Smooth-On, Inc.). The nickel titanium alloy wires are placed along the dorsal aspect of the fingers and are anchored to the palm shell close to the MCP joints at the dorsal surface of the hand. The nickel titanium alloy wires are placed along both sides of the finger to improve stability during motion and to help keep the phalange rings and the cap aligned on the finger. Two silicone bands are used in the one experimental embodiment. One band is used for passive abduction of the CMC and another band is used to secure the palm shell to the hand. The palm silicone band contains two insertion points to route the flexion tendon pairs of the index finger and middle finger down the center of the palm to the actuators. During human subject testing, it was observed that a rigid support structure placed across the palm can cause tissue to accumulate on the palm under the MCP joint of the finger during flexion, which impedes MCP joint displacement. The palm silicone band can deform with the palm during finger motion and thus, avoids tissue buildup and does not restrict the motion of the MCP joint.

To satisfy the requirements of an intuitive and user-friendly interface as well as system portability, the experimental embodiment uses discrete, task-based voice control for device operation. The voice control employed by the experimental embodiment was made compact by requiring only a smartphone (such as Galaxy S8, available from Samsung Electronics Co., Ltd) for onboard signal processing and a Bluetooth Low Energy (BLE) capable microcontroller (SAM3X8E, available from Microchip Technology Inc.) for controlling the actuators.

The app employed with the experimental embodiment used continuous voice control through continuous speech recognition. This allows the experimental embodiment to operate as a hands-free device so that the user does not need to divide their attention between the rehabilitation task and the smartphone.

Since a discrete, task-based controller was used, the user can create a customized dictionary to define exoskeleton actuation for different actions. For example, the user can identify the "cup" and "mug" objects as well as the "Grab" action. Then, different hand configurations can be assigned to "Grab the cup" and "Grab the mug." Thus, commands containing different keywords will actuate the fingers uniquely The joint angles of the fingers for different actions are preset through the use of motor encoders. To begin device operation, the user gives a command to the app. The command is deciphered through natural language processing and parsed for keywords in the dictionary to identify the intended action. When a recognized command is detected, the relevant course of action is started by sending a unique identifier corresponding to the command from the app to the microcontroller via BLE. Alternately, since the experimental embodiment uses continuous voice control, the user can tell the app to "Stop Listening," wherein the app will ignore all further commands until the user says "Resume Listening" to continue exoskeleton control. The keywords determine the joint angles and hand pose associated with the action to be performed. For example, grabbing a block requires a specific set of joint angles for the index finger and the thumb as well as the "Thumb adducted pinch" hand pose. By separating actions into the constituent joint angles and hand pose, the experimental embodiment can classify different actions as requested by the user, simplifying the process of creating user-specific commands for the exoskeleton.

Figure 10:
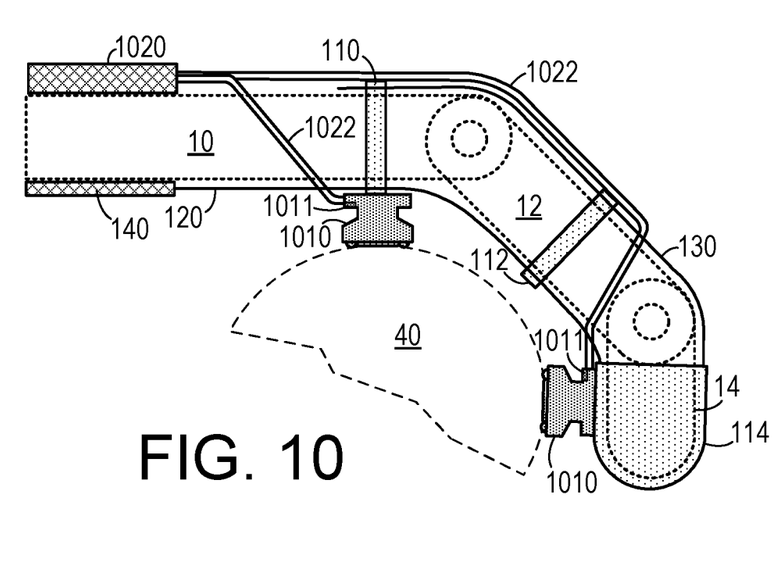
FIG. 10 is a schematic diagram showing an embodiment employing suction cups.
Figure 11A:
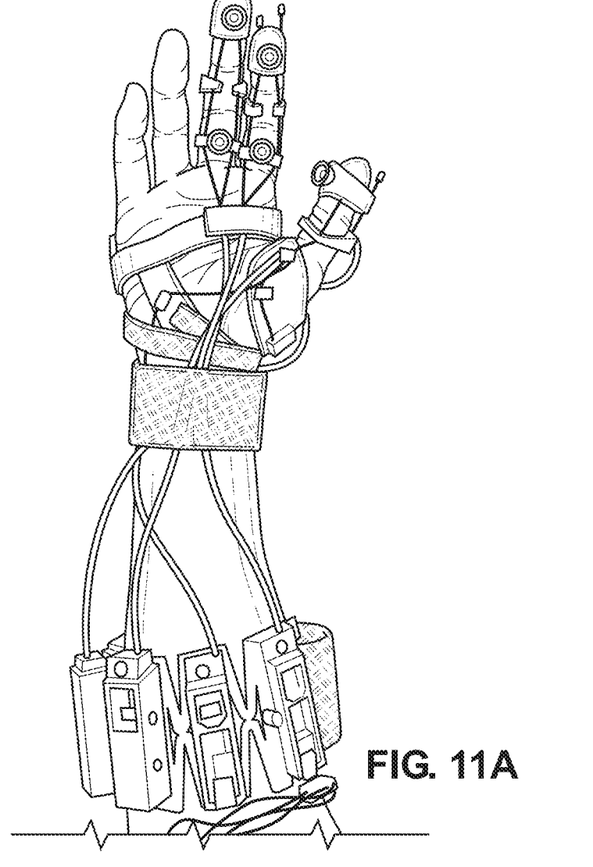
FIGS. 11A-11B are views of an exoskeleton employing suction cups applied to a human hand.
Figure 11B:
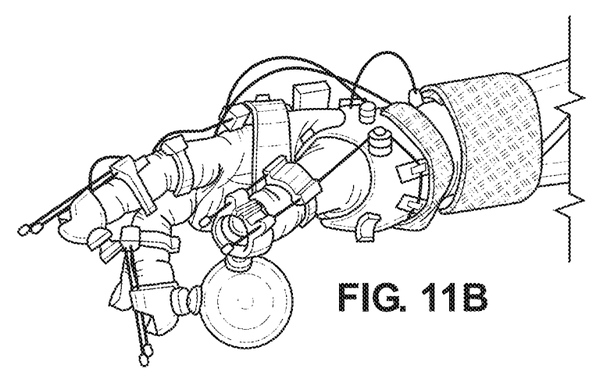

In certain embodiments, the caps 114 can be given tactile surfaces to facilitate grabbing. Also, as shown in FIGS. 10 and 11A-11B, controllable suction cups 1010 can be affixed to the caps 114 and other parts of the system. Such suction cups 1010 can be controlled so that decreased amounts of suction are applied as the user builds up grabbing strength. Suction in the suction cups 1010 can be controlled by a suction controller 1020 that maintains suction at a predetermined amount by pumping air from the suction cups 1010 through pneumatic tubes 1022. Force sensors may be embedded in the base of the suction cups 1010 to provide real time feedback to the suction controller 1020 so as to maintain a desired level of suction. This view shows the suction cups 1010 assisting in gripping an object 40. If the device is used as a rehabilitation device then the suction pressure can be decreased over time as the subject gets better during the rehabilitation regimen. Alternatively, if the device is used as an assist device then the suction will be engaged all the time when needed. Hence, through the voice command and the task requirement, like lifting an iron object versus an egg will lead to varying magnitudes of suction force to lift/manipulate the object. Hence, based on the voice command given the system should adapt the suction pressure. One example of a suction cup-type gripper is disclosed in U.S. Pat. No. 8,382,174, which is incorporated herein by reference. One embodiment employs sensors 1011 (including pressure sensors, force sensors and other types of sensors, depending on the specific application) at the base of the suction cups for measuring the grasping forces in real-time to control the amount of suction force that is exerted.

Although specific advantages have been enumerated above, various embodiments may include some, none, or all of the enumerated advantages. Other technical advantages may become readily apparent to one of ordinary skill in the art after review of the following figures and description. It is understood that, although exemplary embodiments are illustrated in the figures and described below, the principles of the present disclosure may be implemented using any number of techniques, whether currently known or not. Modifications, additions, or omissions may be made to the systems, apparatuses, and methods described herein without departing from the scope of the invention. The components of the systems and apparatuses may be integrated or separated. The operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. It is intended that the claims and claim elements recited below do not invoke 35 U.S.C. § 112(f) unless the words "means for" or "step for" are explicitly used in the particular claim. The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A joint movement device for selective flexion and extension of a joint having a first joint member having a proximal end and an opposite distal end and a second joint member having a proximal end and an opposite distal end and the joint coupling the distal end of the first joint member to the proximal end of the second joint member so that the second joint member is in a flexural relationship to the first joint member, comprising:
   (a) a tendon, having a first end and an opposite second end, disposed adjacent to a selected side of the first joint member and the second joint member;
   (b) a tendon securing device secured to the distal end of the second joint member to which the tendon is secured;
   (c) at least one phalange ring secured to the first joint member, the at least one phalange ring and the tendon securing device including a tending routing mechanism configured to route the tendon from the tendon securing device through the at least one phalange ring;
   (d) an actuator in a fixed relationship with the first joint member and coupled to the tendon, the actuator configured to selectively pull the tendon inwardly thereto, thereby causing the joint to flex; and
   (e) an elastic member coupled to both the phalange ring and the tendon securing device and not coupled to any actuator and configured to apply a constant extension force to the tendon securing device, thereby causing the joint to extend when the actuator releases the tendon.

2. The joint movement device of claim 1, wherein the actuator comprises:
   (a) a tendon shortening mechanism configured to shorten a portion of the first tendon between the phalange ring and the tendon securing device; and
   (b) a controller configured to activate the tendon shortening mechanism.

3. The joint movement device of claim 2, wherein the first end of the tendon is secured to the cap and wherein the tendon shortening mechanism comprises:
   (a) a housing;
   (b) an electric motor coupled to the housing;
   (c) a threaded member coupled to the motor so as to be rotatable thereby, the threaded member including a continuous spiral root having a pitch corresponding to a diameter of the tendon;
   (d) a nut in threaded relationship with the threaded member, the nut held by the housing so that when the motor rotates the threaded member, the nut moves laterally along the threaded member, the nut defining a passage through which the tendon passes,
      wherein the second end of the tendon is secured to the threaded member so that when the threaded member rotates in a first direction, the tendon is pulled into the housing and wrapped around the continuous spiral root and so that when the threaded member rotates in a second direction, opposite the first direction, the tendon is unwrapped from the continuous spiral root and released from the housing.

4. The joint movement device of claim 2, wherein the tendon shortening mechanism comprises an electric motor including a rotor to which both the first end of the tendon and the second end of the tendon are affixed, wherein the tendon is routed through the phalange ring and the tendon securing device so that when the motor rotates in a first direction, a first portion of the tendon and a second portion of the tendon twist about each other so as to cause shortening of a third portion of the tendon disposed between the phalange ring and the tendon securing device and a fourth portion of the tendon disposed between the first phalange ring and the tendon securing device.

5. The joint movement device of claim 1, wherein the elastic member comprises a nickel titanium alloy wire.

6. The joint movement device of claim 1, wherein the tending routing mechanism of each phalange ring includes a passage defined through which the tendon passes that is lined with a poly(tetrafluoroethylene) liner so as to reduce friction on the tendon.

7. The joint movement device of claim 1, wherein the elastic member comprises a spring having one end in a fixed relationship with the first joint and a second end coupled to a cord that is coupled to the cap and that is disposed on a side of the joint opposite from the tendon.

8. An exoskeleton system configured for use with a plurality of different fingers of a hand comprising a plurality of joint movement devices as recited in claim 1, wherein each of the plurality of joint movement devices is secured to a different corresponding finger of the hand, so that each joint movement device is configured to cause the corresponding finger to move in a predetermined manner.

9. The exoskeleton system of claim 8, further comprising a controller that is in control communication with each actuator, wherein the controller is configured to respond to a plurality of different voice commands regarding flexion and extension of the joint.

10. The exoskeleton system of claim 9, wherein each of the plurality of voice commands corresponds to a different predetermined movement pattern for the fingers.

11. The exoskeleton system of claim 10, wherein the different predetermined movement patterns include: gripping an object, pinching the object, grasping the object and releasing the object.

12. The exoskeleton system of claim 9, wherein the controller includes a chipset that is in communication with a digital device.

13. The exoskeleton system of claim 12, wherein the digital device is a selected one of: a mobile telephone, a tablet, a dedicated device, a desktop computer and a laptop computer.

14. A robotic exoskeleton configured for use with a plurality of different fingers of a hand, having a palm, each finger having at least one joint including a first joint member having a proximal end and an opposite distal end and a second joint member having a proximal end and an opposite distal end wherein the second joint member is in a flexural relationship to the first joint member, the robotic exoskeleton comprising:
 (a) a plurality of joint movement devices, wherein each of the plurality of joint movement devices is secured to a different corresponding finger of the hand, so that each joint movement device is configured to cause the corresponding finger to move in a predetermined manner, each of the plurality of joint movement devices including:
  (i) a first tendon, having a first end and an opposite second end, disposed adjacent to a selected side of the first joint member and the second joint member;
  (ii) a tendon securing device secured to the distal end of the second joint member to which the tendon is secured;
  (iii) a first phalange ring secured to the first joint member and a second phalange ring secured to the second joint member, the first phalange ring, the second phalange ring, and the tendon securing device including a tending routing mechanism configured to route the tendon from the tendon securing device through the first phalange ring and the second phalange ring;
  (iv) an actuator in a fixed relationship with the first joint member and coupled to the tendon, the actuator configured to selectively pull the tendon inwardly thereto, thereby causing the joint to flex, the actuator including a tendon shortening mechanism configured to shorten a portion of the first tendon between the first phalange ring and the tendon securing device;
  (v) an elastic member coupled to both the first phalange ring and the second phalange ring and not coupled to any actuator and configured to apply a constant extension force to the second phalange ring, thereby causing the joint to extend when the actuator releases the tendon; and
  (vi) a controller in control communication with each actuator and configured to respond to a plurality of different voice commands regarding flexion and extension of each joint.

15. The robotic exoskeleton of claim 14, wherein each of the plurality of voice commands to a different predetermined movement pattern for the fingers.

16. The robotic exoskeleton of claim 15, wherein the different predetermined movement patterns include: gripping an object, pinching the object, grasping the object and releasing the object.

17. The robotic exoskeleton of claim 14, wherein the controller includes a chipset that is in communication with a digital device.

18. The robotic exoskeleton of claim 17, wherein the digital device is a selected one of: a mobile telephone, a tablet, a dedicated device, a desktop computer and a laptop computer.

19. The robotic exoskeleton of claim 14, wherein the first end of each tendon is secured to the cap and wherein the tendon shortening mechanism comprises:
 (a) a housing;
 (b) an electric motor coupled to the housing;
 (c) a threaded member coupled to the motor so as to be rotatable thereby, the threaded member including a continuous spiral root having a pitch corresponding to a diameter of the tendon;
 (d) a nut in threaded relationship with the threaded member, the nut held by the housing so that when the motor rotates the threaded member, the nut moves laterally along the threaded member, the nut defining a passage through which the tendon passes,
 wherein the second end of the tendon is secured to the threaded member so that when the threaded member rotates in a first direction, the tendon is pulled into the housing and wrapped around the continuous spiral root and so that when the threaded member rotates in a second direction, opposite the first direction, the tendon is unwrapped from the continuous spiral root and released from the housing.

20. The robotic exoskeleton of claim 14, wherein the elastic member comprises a nickel titanium alloy wire.

21. The robotic exoskeleton of claim 14, further comprising:
(a) a plurality of suction cups disposed adjacent to the palm so as to increase a gripping force applied to an object being gripped;
(b) a suction cup controller; and
(c) a pneumatic tube coupling each suction cup to the suction cup controller so that the suction cup controller maintains a desired pressure with the suction cup.

22. The robotic exoskeleton of claim 21, further comprising a sensor embedded in at least one of the plurality of suction cups and configured to provide the suction cup controller with real time feedback.

23. A robotic exoskeleton configured for use with a plurality of different fingers of a hand, having a palm, each finger having at least one joint including a first joint member having a proximal end and an opposite distal end and a second joint member having a proximal end and an opposite distal end wherein the second joint member is in a flexural relationship to the first joint member, the robotic exoskeleton comprising:
(a) a plurality of joint movement devices, wherein each of the plurality of joint movement devices is secured to a different corresponding finger of the hand, so that each joint movement device is configured to cause the corresponding finger to move in a predetermined manner, each of the plurality of joint movement devices including:
(i) a first tendon, having a first end and an opposite second end, disposed adjacent to a selected side of the first joint member and the second joint member;
(ii) a tendon securing device secured to the distal end of the second joint member to which the tendon is secured;
(iii) a first phalange ring secured to the first joint member and a second phalange ring secured to the second joint member, the first phalange ring, the second phalange ring, and the tendon securing device including a tending routing mechanism configured to route the tendon from the tendon securing device through the first phalange ring and the second phalange ring;
(iv) an actuator in a fixed relationship with the first joint member and coupled to the tendon, the actuator configured to selectively pull the tendon inwardly thereto, thereby causing the joint to flex, the actuator including a tendon shortening mechanism configured to shorten a portion of the first tendon between the first phalange ring and the tendon securing device; and
(v) an elastic member coupled to both the first phalange ring and the second phalange ring and not coupled to any actuator and configured to apply a constant extension force to the second phalange ring, thereby causing the joint to extend when the actuator releases the tendon;
(b) a controller in control communication with each actuator and configured to respond to a plurality of different voice commands regarding flexion and extension of each joint;
(c) a plurality of suction cups disposed adjacent to the palm so as to increase a gripping force applied to an object being gripped; and
(d) a plurality of sensors disposed adjacent to the palm so as to provide feedback to the controller.

24. A robotic exoskeleton configured for use with a plurality of different fingers of a hand, having a palm, each finger having at least one joint including a first joint member having a proximal end and an opposite distal end and a second joint member having a proximal end and an opposite distal end wherein the second joint member is in a flexural relationship to the first joint member, the robotic exoskeleton comprising:
(a) a plurality of joint movement devices, wherein each of the plurality of joint movement devices is secured to a different corresponding finger of the hand, so that each joint movement device is configured to cause the corresponding finger to move in a predetermined manner, each of the plurality of joint movement devices including:
(i) a first tendon, having a first end and an opposite second end, disposed adjacent to a selected side of the first joint member and the second joint member;
(ii) a tendon securing device secured to the distal end of the second joint member to which the tendon is secured;
(iii) a first phalange ring secured to the first joint member and a second phalange ring secured to the second joint member, the first phalange ring, the second phalange ring, and the tendon securing device including a tending routing mechanism configured to route the tendon from the tendon securing device through the first phalange ring and the second phalange ring;
(iv) an actuator in a fixed relationship with the first joint member and coupled to the tendon, the actuator configured to selectively pull the tendon inwardly thereto, thereby causing the joint to flex, the actuator including a tendon shortening mechanism configured to shorten a portion of the first tendon between the first phalange ring and the tendon securing device; and
(v) an elastic member coupled to both the first phalange ring and the second phalange ring and not coupled to any actuator and configured to apply a constant extension force to the second phalange ring, thereby causing the joint to extend when the actuator releases the tendon;
(b) a controller in control communication with each actuator and configured to respond to a plurality of different voice commands regarding flexion and extension of each joint; and
(c) a plurality of suction cups disposed adjacent to the palm so as to increase a gripping force applied to an object being gripped.

25. A robotic exoskeleton configured for use with a plurality of different fingers of a hand, having a palm, each finger having at least one joint including a first joint member having a proximal end and an opposite distal end and a second joint member having a proximal end and an opposite distal end wherein the second joint member is in a flexural relationship to the first joint member, the robotic exoskeleton comprising:
(a) a plurality of joint movement devices, wherein each of the plurality of joint movement devices is secured to a different corresponding finger of the hand, so that each joint movement device is configured to cause the corresponding finger to move in a predetermined manner, each of the plurality of joint movement devices including:
(i) a first tendon, having a first end and an opposite second end, disposed adjacent to a selected side of the first joint member and the second joint member;

(ii) a tendon securing device secured to the distal end of the second joint member to which the tendon is secured;

(iii) a first phalange ring secured to the first joint member and a second phalange ring secured to the second joint member, the first phalange ring, the second phalange ring, and the tendon securing device including a tending routing mechanism configured to route the tendon from the tendon securing device through the first phalange ring and the second phalange ring;

(iv) an actuator in a fixed relationship with the first joint member and coupled to the tendon, the actuator configured to selectively pull the tendon inwardly thereto, thereby causing the joint to flex, the actuator including a tendon shortening mechanism configured to shorten a portion of the first tendon between the first phalange ring and the tendon securing device; and (v) an elastic member coupled to both the first phalange ring and the second phalange ring and not coupled to any actuator and configured to apply a constant extension force to the second phalange ring, thereby causing the joint to extend when the actuator releases the tendon;

(b) a controller in control communication with each actuator and configured to respond to a plurality of different voice commands regarding flexion and extension of each joint; and (c) a plurality of sensors disposed adjacent to the palm so as to provide feedback to the controller.

* * * * *